(12) United States Patent
Deshpande et al.

(10) Patent No.: US 7,777,039 B2
(45) Date of Patent: Aug. 17, 2010

(54) PROCESS FOR THE PREPARATION OF ARIPIPRAZOLE

(75) Inventors: Pandurang Balwant Deshpande, Vadodara (IN); Parven Kumar Luthra, Vadodara (IN); Ashok Prataprai Shanishchara, Vadodara (IN); Ramesh Manepalli, Vadodara (IN); Dharmesh Balvantrai Mistry, Vadodara (IN)

(73) Assignee: Alembic Limited, Gujarat (IN)

( * ) Notice: Subject to any disclaimer, the term of this patent is extended or adjusted under 35 U.S.C. 154(b) by 1106 days.

(21) Appl. No.: 11/448,504

(22) Filed: Jun. 7, 2006

(65) Prior Publication Data

US 2006/0258869 A1    Nov. 16, 2006

(30) Foreign Application Priority Data

Apr. 3, 2006    (IN)    .................. 507/MUM/2006

(51) Int. Cl.
*C07D 215/38*    (2006.01)
(52) U.S. Cl. ...................................... 546/159
(58) Field of Classification Search .................. 546/159
See application file for complete search history.

(56) References Cited

OTHER PUBLICATIONS

Li, CA143:172893, abstract only of CN 1513838, Jul. 2004.*

* cited by examiner

*Primary Examiner*—D. Margaret Seaman

(57) ABSTRACT

The present invention relates to an improved process for the preparation of 7-[4-[4-(2,3-dichlorophenyl)piperazin-1-yl] butoxy]-1,2,3,4-tetrahydroquinolin-2-one (Aripiprazole) having dimer impurity less than 0.15%, particularly, the present invention relates to an improved process for the preparation of 7-(4-chlorobutoxy)-3,4-dihydrocarbostyril of formula (I) having dimer impurity less than 0.5%

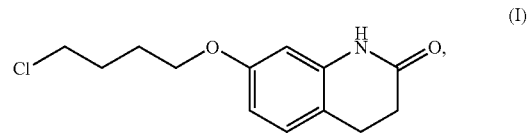

which includes a step of reacting 7-hydroxy-tetrahydroquinolinone of formula (III)

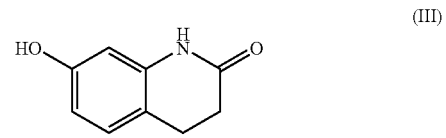

with 1-bromo-4-chlorobutane in the presence of a base in a solvent.

8 Claims, No Drawings

PROCESS FOR THE PREPARATION OF ARIPIPRAZOLE

FIELD OF THE INVENTION

The present invention relates to an improved process for the preparation of 7-[4-[4-(2,3-dichlorophenyl)piperazin-1-yl] butoxy]-1,2,3,4-tetrahydroquinolin-2-one (Aripiprazole) having dimer impurity of compound of formula (V), Formula V

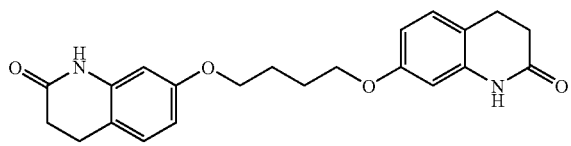

less than 0.15%. Particularly, the present invention relates to an improved process for the preparation of 7-(4-chlorobutoxy)-3,4-dihydrocarbostyril of formula (I) having dimer impurity less than 0.5%.

(I)

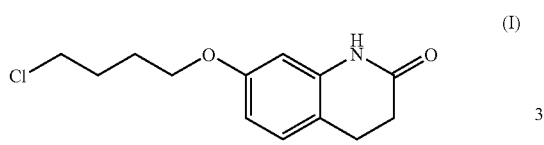

BACKGROUND OF THE INVENTION

The chemical name of Aripiprazole is 7-[4-[4-(2,3-dichlorophenyl)piperazin-1-yl] butoxy]-1,2,3,4-tetrahydroquinolin-2-one and molecular formula is $C_{23}H_{27}Cl_2N_3O_2$ and molecular weight is 448.39. Aripiprazole is represented by structural formula (II)

(II)

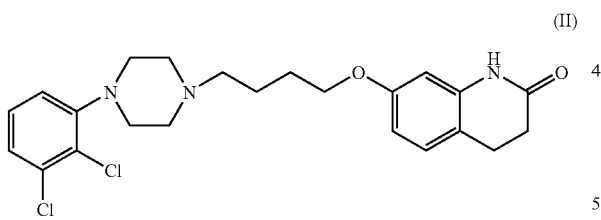

Aripiprazole is marketed by Bristol Myers Squibb under tradename Abilify® and is indicated for the treatment of Alzheimer's dementia, antipsychotic disorders and bipolar disorders.

7-[4-[4-(2,3-dichlorophenyl)piperazin-1-yl]butoxy]-1,2,3,4-tetrahydroquinolin-2-one exhibits high affinity for dopamine $D_2$ and $D_3$, serotonin $5-HT_{1A}$ and $5-HT_{2A}$ receptors, moderate affinity for dopamine $D_4$, serotonin $5-HT_{2C}$ and $5-HT_7$, alpha-1-adrenergic and histamine $H_1$ receptors. Aripiprazole functions as a partial agonist at the dopamine $D_2$ and the serotonin $5-HT_{1A}$ receptors, and as an antagonist at serotonin $5-HT_{2A}$ receptor.

7-[4-[4-(2,3-dichlorophenyl)piperazin-1-yl]butoxy]-1,2,3,4-tetrahydroquinolin-2-one, namely Aripiprazole, is broadly disclosed in U.S. Pat. No. 4,734,416 and specifically disclosed in U.S. Pat. No. 5,006,528. The process for the preparation of 7-[4-[4-(2,3-dichlorophenyl)piperazin-1-yl]butoxy]-1,2,3,4-tetrahydroquinolin-2-one is well disclosed in U.S. Pat. No. 5,006,528.

U.S. Pat. No. 5,006,528 provides a process for the preparation of 7-(4-bromobutoxy)-3,4-dihydrocarbostyril of formula (I') in water in basic conditions. Water can often be difficult to remove from reaction mixtures. Moreover, 7-(4-bromobutoxy)-3,4-dihydrocarbostyril obtained by this process involves the formation of high level of dimer impurity, which causes low yield and also affects the purity of intermediate as well as purity of the final product.

Scheme-1

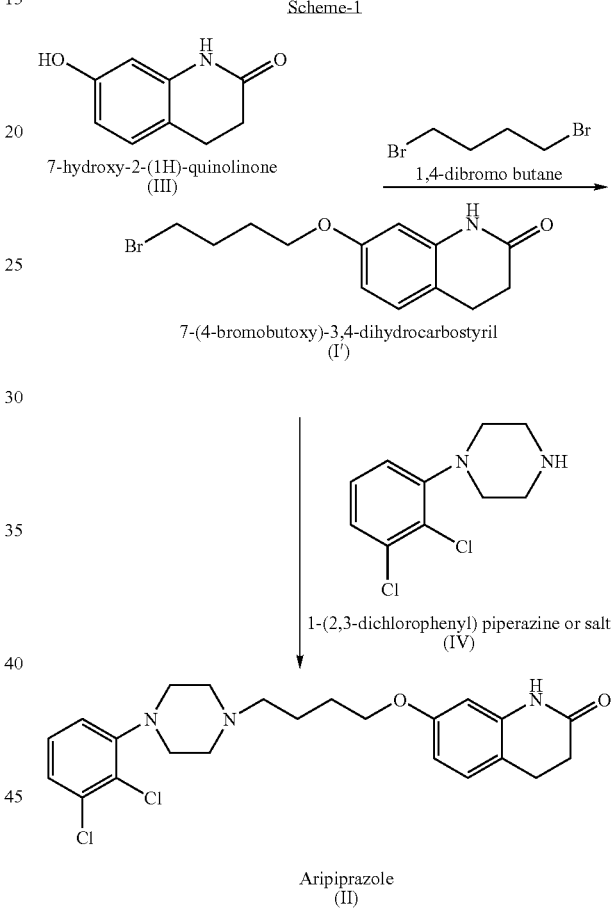

Journal of Medicinal Chemistry, Vol. 41, No. 5, 658-667, 1998 discloses the preparation of 7-(4-bromobutoxy)-3,4-dihydrocarbostyril by alkylation of 7-hydroxy-tetrahydroquinolinone with 1,4-dibromobutane in the presence of potassium carbonate in N,N-dimethylformamide (DMF).

The recovery of DMF can be very difficult. Moreover, DMF is harmful by inhalation, ingestion or skin contact. It may act as a carcinogen and long-term exposure may result in kidney or liver damage. Moreover, 7-(4-bromobutoxy)-3,4-dihydrocarbostyril obtained by this process involves the formation of dimer impurity in the range of 5-8%, which causes low yield and affects the purity 7-(4-bromobutoxy)-3,4-dihydrocarbostyril as well as final product i.e. Aripiprazole.

Most of the process known in the art utilizes 7-(4-bromobutoxy)-3,4-dihydrocarbostyril of formula (I') as an intermediate for the preparation of Aripiprazole. However, preparation of this intermediate by the method known in the art results in a compound having high content of the dimer impurity (5-8%).

Therefore, Aripiprazole prepared by using 7-(4-bromobutoxy)-3,4-dihydrocarbostyril of formula (I') having dimer impurity of 5-8% would not give the final compound of desired yield and purity specifically the content of dimer impurity.

Moreover, the content of undesired impurity in the final product is always a cause of concern with respect to Food and Drug Authorities (FDA) requirement. Therefore, it is required to have the undesired impurity content well below the level specified in the International Conference on Harmonization (ICH) guideline as per regulatory authority. Particularly with respect to the known impurity the acceptable limit 0.15%. Therefore it is extremely important to control the level of dimer impurity to comply with the regulatory requirement.

In summary, process disclosed in prior art for the preparation of 7-(4-bromobutoxy)-3,4-dihydrocarbostyril, are tedious and requires laborious column chromatography.

Moreover, 7-(4-bromobutoxy)-3,4-dihydrocarbostyril obtained by prior art process, involves the formation of dimer impurity, which causes low yield and purity.

Therefore, there is a need to develop a process which provides an intermediate of high purity specifically with less content of dimer impurity which is difficult to control as per the method know in the art.

With an objective of reducing the content of dimer impurity from the intermediate, the present inventors has directed the research work towards developing a process for preparing of 7-(4-chlorobutoxy)-3,4-dihydrocarbostyril having dimer impurity less than 0.5%

The present inventors had tried reaction of 7-hydroxy-tetrahydroquinolinone with 1,4-dibromobutane in the presence of a base in several solvent such as dimethylformamide, methylene dichloride, water or tetrahydrofuran to achieve the desired purity of 7-(4-bromobutoxy)-3,4-dihydrocarbostyril but the present inventors did not get desired purity due to the presence of dimer impurity of formula (V) up to 10%.

Formula V

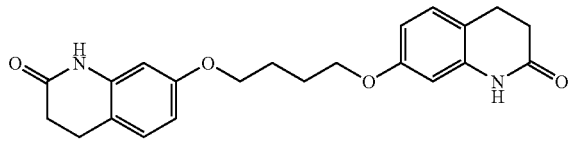

Surprisingly, when present inventors had carried out the reaction of 7-hydroxy-tetrahydroquinolinone with selectively using 1-bromo-4-chlorobutane in the presence of a base and a solvent to obtain 7-(4-chlorobutoxy)-3,4-dihydrocarbostyril, compound obtained with high yield, purity of the compound was more than 98% and the content of dimer impurity was substantially reduced i.e. less than 0.5%. Subsequently, when Aripiprazole is prepared by using this intermediate i.e. 7-(4-chlorobutoxy)-3,4-dihydrocarbostyril having dimer impurity less than 0.5%, the purity and yield of the final product is substantially improved and the dimer content was drastically reduced to 0.05% which is well accepted by international regulatory norms specifically USFDA.

The present inventors have found that due to significant decrease in dimer impurity, yield and purity of 7-(4-chlorobutoxy)-3,4-dihydrocarbostyril improves which subsequently leads to improvement in the quality of Aripiprazole. Moreover, this makes the process for the preparation of Aripiprazole operationally simple and easily applicable at an industrial scale.

Therefore, the present invention is specifically directed towards the selective use of 1-bromo-4-chlorobutane, which significantly reduces the unwanted dimer impurity and provides 7-(4-chlorobutoxy)-3,4-dihydrocarbostyril of formula (I) with high yield and purity of more than 98% and having dimer impurity less than 0.5% which in turn helps in improving the quality of resultant compound i.e. Aripiprazole.

OBJECT OF THE INVENTION

Therefore, it is an object of the invention is to provide improved process for the preparation of 7-(4-chlorobutoxy)-3,4-dihydrocarbostyril having dimer impurity less than 0.5%.

Another object of the invention is to provide process for the preparation of 7-[4-[4-(2,3-dichlorophenyl)piperazin-1-yl]butoxy]-1,2,3,4-tetrahydroquinolin-2-one having dimer impurity less than 0.15%.

A further object of the invention is to provide process for the preparation of 7-[4-[4-(2,3-dichlorophenyl)piperazin-1-yl]butoxy]-1,2,3,4-tetrahydroquinolin-2-one having dimer impurity less than 0.05%.

A further object of the present invention is to provide an improved process for preparing preparation of 7-(4-chlorobutoxy)-3,4-dihydrocarbostyril, which control the dimer impurity.

A yet another object of the present invention is to provide an improved process for the preparation of 7-(4-chlorobutoxy)-3,4-dihydrocarbostyril of formula (I) having dimer impurity less than 0.5%.

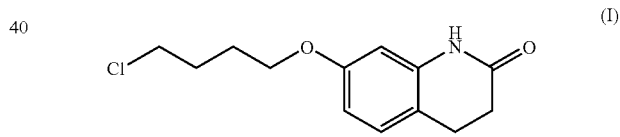

comprising a step of, reacting 7-hydroxy-tetrahydroquinolinone of formula (III)

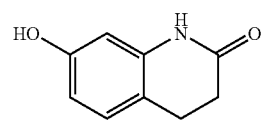

with 1-bromo-4-chlorobutane in the presence of a base in a solvent.

DETAILED DESCRIPTION OF THE INVENTION

Accordingly, the present invention relates to an improved process for the preparation of 7-(4-chlorobutoxy)-3,4-dihydrocarbostyril of formula (I) having dimer impurity less than 0.5%

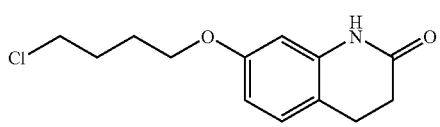

(I)

comprising a step of, reacting 7-hydroxy-tetrahydroquinolinone of formula (III)

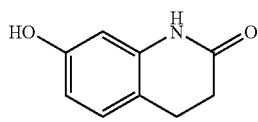

(III)

with 1-bromo-4-chlorobutane in the presence of a base in a solvent.

In a preferred embodiment of the present invention, the reaction of 7-hydroxy-tetrahydroquinolinone with 1-bromo-4-chlorobutane in the presence of a sodium hydroxide in dimethylacetamide is carried out at ambient temperature.

After completion of the reaction, the reaction mixture is cooled at ambient temperature and demineralise water is added to it. The reaction mixture is extracted with ethylacetate. Organic layer is separated and washed with 5% brine and finally dried over sodium sulphate. The organic layer is evaporated to dryness optionally under reduced pressure at 45° C. to obtain residue. The residue obtained is treated with cyclohexane to give 7-(4-chlorobutoxy)-3,4-dihydrocarbostyril.

The examples of the base mentioned hereinabove include but not limited to NaOH, KOH, $Ca(OH)_2$, $Na_2CO_3$, $K_2CO_3$ or $NaHCO_3$. The preferable base is NaOH.

The examples of the solvent mentioned hereinabove include but not limited to ethers such as dioxane, tetrahydrofuran, ethylene glycol dimethyl ether and the like or mixture thereof; aromatic hydrocarbons such as toluene, xylene and the like or mixture thereof; lower alcohols such as methanol, ethanol, isopropanol and the like or mixture thereof; polar solvents such as dimethylformamide (DMF), dimethyl sulfoxide (DMSO), acetonitrile, dimethylacetamide and the like or mixture thereof.

Subsequently, 7-(4-chlorobutoxy)-3,4-dihydrocarbostyril of formula (I) can be converted into Aripiprazole by method known in the art.

Following is the comparison of the result of intermediate i.e. 7-(4-chlorobutoxy)-3,4-dihydrocarbostyril of formula (I) as prepared by the present invention vis-à-vis intermediate i.e. 7-(4-bromobutoxy)-3,4-dihydrocarbostyril by 1,4-dibromobutane as prepared by the process as disclosed in prior art.

TABLE 1

| S. No. | Process | Yield (%) | Purity (%) | Dimer content (%) |
|---|---|---|---|---|
| 1 | Preparation of intermediate i.e. 7-(4-bromobutoxy)-3,4-dihydrocarbostyril by 1,4-dibromobutane as per prior art | 66.8 | 92 | 5.0–8.0 |
| 2 | Preparation of intermediate i.e. 7-(4-chlorobutoxy)-3,4-dihydrocarbostyril by | 80.0 | 99 | less than 0.5 |

TABLE 1-continued

| S. No. | Process | Yield (%) | Purity (%) | Dimer content (%) |
|---|---|---|---|---|
|  | 1-bromo-4-chlorobutane as per the present invention |  |  |  |

Following is the comparison of the result of Aripiprazole as prepared by the present invention vis-à-vis Aripiprazole as prepared by the process as disclosed in prior art

TABLE 2

| S. No. | Process | Yield (%) | Purity (%) | Dimer content (%) |
|---|---|---|---|---|
| 1 | Preparation of Aripiprazole using 7-(4-bromobutoxy)-3,4-dihydrocarbostyril as per the prior art | 78–82 | 98% | 0.5 |
| 2 | Preparation of Aripiprazole using 7-(4-chlorobutoxy)-3,4-dihydrocarbostyril as per the present invention | 90–92 | More than 99 | less than 0.05 |

The results clearly depicts that the selective use of 1-bromo-4-chlorobutane significantly improves the purity and yield of the intermediate and also substantially reduces the dimer impurity not only in the intermediate but also in the final product i.e. Aripiprazole.

In another embodiment of the present invention is to provide an improved process for the preparation of 7-[4-[4-(2,3-dichlorophenyl)piperazin-1-yl]butoxy]-1,2,3,4-tetrahydroquinolin-2-one of formula (II) having impurity less than 0.15%

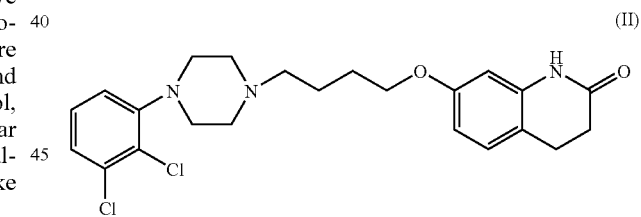

(II)

comprising steps of, a) reacting 7-hydroxy-tetrahydroquinolinone of formula (III)

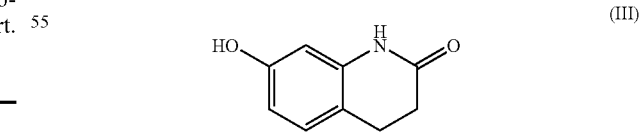

(III)

with 1-bromo-4-chlorobutane in the presence of a base in a solvent to obtain 7-(4-chlorobutoxy)-3,4-dihydrocarbostyril of formula (I) having dimer impurity less than 0.5%.

b) condensing 7-(4-chlorobutoxy)-3,4-dihydrocarbostyril of formula (I) having dimer impurity less than 0.5%

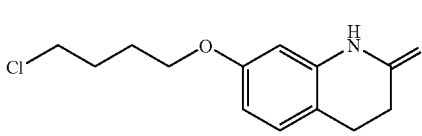

with 1-(2,3-dichlorophenyl)piperazine of formula (IV) or salt thereof,

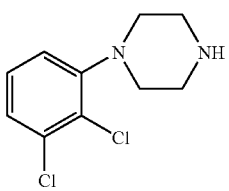

in the presence of a base, a phase transfer catalyst and sodium iodide in a solvent.

In a preferred embodiment of the present invention, the condensation of 7-(4-chlorobutoxy)-3,4-dihydrocarbostyril which as prepared by present invention, with 1-(2,3-dichlorophenyl)piperazine hydrochloride in the presence of a potassium carbonate, tetrabutylammonium bromide and sodium iodide as the reaction accelerator in acetonitrile is carried out at reflux temperature.

The reaction mixture is refluxed and maintained at reflux until reaction completes. The reaction mass is cooled at room temperature. Water is added to reaction mass and stirred for 30 min at ambient temperature. The mass is filtered and washed with water till pH of filtrate come to 7.0-7.5. The solid is dried at 60° C. to give Aripiprazole.

The examples of the base mentioned hereinabove in step (b) include but not limited to an inorganic base such as potassium carbonate, calcium carbonate, sodium carbonate, sodium hydroxide, sodium hydrogen carbonate, sodium amide, sodium hydride and the like or mixture thereof; and an organic base such as triethylamine, tripropylamine, pyridine, quinoline and the like or mixture thereof.

The examples of the solvent mentioned hereinabove in step (b) include but not limited to ethers such as dioxane, tetrahydrofuran, ethylene glycol dimethyl ether and the like or mixture thereof; aromatic hydrocarbons such as toluene, xylene and the like or mixture thereof; lower alcohols such as methanol, ethanol, isopropanol and the like or mixture thereof; polar solvents such as dimethylformamide (DMF), dimethyl sulfoxide (DMSO), acetonitrile, dimethylacetamide and the like or mixture thereof.

The examples of the reaction accelerator mentioned hereinabove in step (b) include but not limited to an alkali metal iodide such as potassium iodide, sodium iodide.

The examples of the phase transfer catalyst mentioned hereinabove in step (b) include but not limited to tetrabutylammonium bromide (TBAB), tetrabutylammonium hydroxide, TEBA, tricaprylylmethylammonium chloride, dodecyl sulfate sodium salt, tetrabutylammonium hydrogensulfate, hexadecyl tributyl phosphonium bromide, or hexadecyl trimethyl ammonium bromide.

During condensation, the use of 7-(4-chlorobutoxy)-3,4-dihydrocarbostyril instead of 7-(4-bromobutoxy)-3,4-dihydrocarbostyril reduces the dimer impurity and provides Aripiprazole having dimer impurity 0.15%.

The present invention provides process of preparation of 7-(4-chlorobutoxy)-3,4-dihydrocarbostyril of formula (I), which is simple, environment friendly, economical and leads to an enhanced purity.

The process of the present invention is described by the following examples, which are illustrative only and should not be construed so as to limit the scope of the invention in any manner.

EXAMPLE 1

Preparation of
7-(4-bromobutoxy)-3,4-dihydrocarbostyril 1,4-dibromo butane (509 ml) was added to a stirred solution of 7-hydroxy-3,4-dihydrocarbostyril (100 gm) in dimethylacetamide (500 ml) at ambient temperature. The reaction mixture was heated at 36° to 40° C. Sodium hydroxide (33.1 gm) was added to the reaction mixture at the interval of 30 min (Complete the addition of sodium hydroxide in 9 equal fractions in 4.0 hours). The reaction mixture was cooled at ambient temperature and D.M Water was added to it. The reaction mixture was extracted with ethylacetate. Organic layer was separated and washed with 5% brine and finally dried over sodium sulphate. The organic layer was evaporated to dryness under reduced pressure (10 mm) at 45° C. to obtain residue. To the residue cyclohexane (1000 ml) was added to give of 7-(4-bromobutoxy)-3,4-dihydrocarbostyril.

Yield: 122.0 gms (66.8%)
Dimer content: 5.0-8.0%

EXAMPLE 2

Preparation of
7-(4-chlorobutoxy)-3,4-dihydrocarbostyril 1-bromo-4-chloro butane (500 ml) was added to a stirred solution of 7-hydroxy-3,4-dihydrocarbostyril (100 gm) in dimethylacetamide (500 ml) at ambient temperature. The reaction mixture was heated at 36° to 40° C. Sodium hydroxide (33.1 gm) was added to the reaction mixture at the interval of 30 min (Complete the addition of sodium hydroxide in 9 equal fractions in 4.0 hours). The reaction mixture was cooled at ambient temperature and D.M Water was added to it. The reaction mixture was extracted with ethylacetate. Organic layer was separated and washed with 5% brine and finally dried over sodium sulphate. The organic layer was evaporated to dryness under reduced pressure (10 mm) at 45° C. to obtain residue. To the residue cyclohexane (1000 ml) was added to give of 7-(4-chlorobutoxy)-3,4-dihydrocarbostyril.

Yield: 124.0 gm (80.0%)
Dimer content: 0.3-0.5%.

EXAMPLE 3

Preparation of 7-[4-[4-(2,3-dichlorophenyl)piperazin-1-yl]butoxy]-1,2,3,4-tetrahydro quinolin-2-one (Aripiprazole) (7-CQ Route)

A mixture of 100 gm 7-(4-chloro butoxy)-3,4-Dihydrocarbostyril in 600 ml acetonitrile with sodium iodide (88.6 gm), $K_2CO_3$ (109 gm), Tetrabutylammonium bromide (TBAB) (0.5 gm) and 1-(2,3-dichlorophenyl)piperazine hydrochloride (110 gm) was stirred at ambient temperature. The reaction mixture was refluxed and maintained at reflux until reaction completes. The reaction mass was cooled at room temperature. DM Water (500 ml) was added to reaction mass and stirred for 30 min at ambient temperature. The mass was filtered and washed with water till pH of filtrate came to 7.0-7.5. The solid was dried in hot air oven at 60° C. to give Aripiprazole.

Yield (%): 159.6 gm (90%)
Purity by HPLC ~99.2%
Dimer content ~0.05%

The invention claimed is:

1. A process for the preparation of 7-(4-chlorobutoxy)-3,4-dihydrocarbostyril of formula (I) having dimer impurity in an amount of less than 0.5%

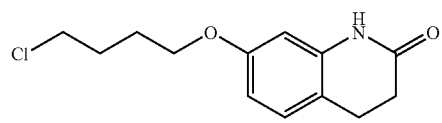
(I)

comprising a step of reacting 7-hydroxy-tetrahydroquinolinone of formula (III)

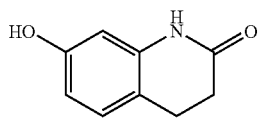
(III)

with 1-bromo-4-chlorobutane in the presence of a base in dimethylacetamide.

2. A process according to claim 1, wherein the base is at least one selected from the group consisting of NaOH, KOH, Ca(OH)$_2$, Na$_2$CO$_3$, K$_2$CO$_3$, and NaHCO$_3$.

3. A process for the preparation of 7-[4-[4-(2,3-dichlorophenyl)piperazin-1-yl] butoxy]-1,2,3,4-tetrahydroquinolin-2-one of formula (II) having dimer impurity in an amount of less than 0.15%

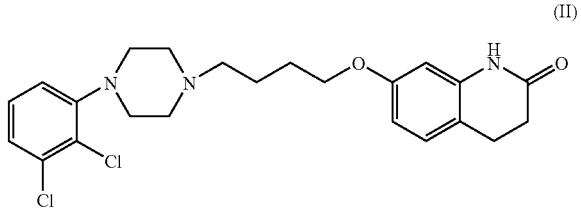
(II)

comprising steps of:
a) reacting 7-hydroxy-tetrahydroquinolinone of formula (III)

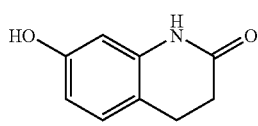
(III)

with 1-bromo-4-chlorobutane in the presence of a base in a solvent to obtain 7-(4 chlorobutoxy)-3,4-dihydrocarbostyril of formula (I) having dimer impurity in an amount of less than 0.5%; and b) condensing 7-(4-chlorobutoxy)-3,4-dihydrocarbostyril of formula (I) having dimer impurity in an amount of less than 0.5%

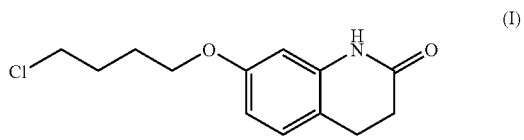
(I)

with 1-(2,3-dichlorophenyl)piperazine of formula (IV) or salt thereof,

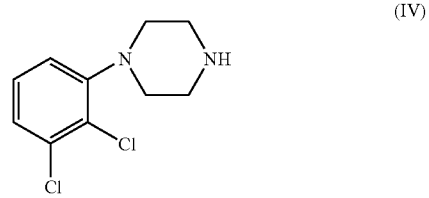
(IV)

in the presence of a base, a phase transfer catalyst, and sodium iodide in a solvent.

4. A process according to claim 3, wherein the base in step (a) is at least one selected from the group consisting of NaOH, KOH, Ca(OH)$_2$, Na$_2$CO$_3$, K$_2$CO$_3$, and NaHCO$_3$.

5. A process according to claim 3, wherein the solvent in step (a) is dimethylacetamide.

6. A process according to claim 3, wherein the base in step (b) is at least one selected from the group consisting of an inorganic base, which is at least one selected from the group consisting of potassium carbonate, calcium carbonate, sodium carbonate, sodium hydroxide, sodium hydrogen carbonate, sodium amide, sodium hydride, and a mixture thereof; and an organic base, which is at least one selected from the group consisting of triethylamine, tripropylamine, pyridine, quinoline, and a mixture thereof.

7. A process according to claim 3, wherein the solvent in step (b) is at least one selected from a group consisting of dioxane, tetrahydrofuran, ethylene glycol dimethyl ether, toluene, xylene, methanol, ethanol, isopropanol, dimethylformamide (DMF), dimethylsulfoxide (DMSO), acetonitrile, dimethylacetamide, and a mixture thereof.

8. A process according to claim 3, wherein the phase transfer catalyst in step (b) is at least one selected from group consisting of tetrabutylammonium bromide, tetrabutylammonium hydroxide, TEBA, tricaprylylmethylammonium chloride, dodecyl sulfate, sodium salt, tetrabutylammonium hydrogensulfate, hexadecyl tributyl phosphonium bromide, and hexadecyl trimethyl ammonium bromide.

* * * * *